United States Patent
Grass et al.

(10) Patent No.: US 6,823,204 B2
(45) Date of Patent: Nov. 23, 2004

(54) METHOD OF IMAGING THE BLOOD FLOW IN A VASCULAR TREE

(75) Inventors: Michael Grass, Hamburg (DE); Holger Schmitt, Hassersheim (DE); Volker Rasche, Hamburg (DE)

(73) Assignee: Koninklijke Philips Electronics N.V., Eindhoven (NL)

(*) Notice: Subject to any disclaimer, the term of this patent is extended or adjusted under 35 U.S.C. 154(b) by 1 day.

(21) Appl. No.: 10/221,240

(22) PCT Filed: Dec. 21, 2001

(86) PCT No.: PCT/IB01/02699
§ 371 (c)(1),
(2), (4) Date: Sep. 9, 2002

(87) PCT Pub. No.: WO02/056260
PCT Pub. Date: Jul. 18, 2002

(65) Prior Publication Data
US 2003/0040669 A1 Feb. 27, 2003

(30) Foreign Application Priority Data
Jan. 9, 2001 (DE) .......................... 101 00 572

(51) Int. Cl.⁷ .................................................. A61B 5/05
(52) U.S. Cl. ........................ 600/407; 600/410; 600/419; 600/421; 600/425; 382/123; 382/131; 382/132; 378/4; 378/21; 378/23; 378/62
(58) Field of Search .................................. 600/407, 409, 600/425, 410, 419, 421; 382/128, 131, 132; 378/4, 21–27, 62, 66, 67, 8, 41

(56) References Cited

U.S. PATENT DOCUMENTS

| | | | | |
|---|---|---|---|---|
| 6,246,784 B1 * | 6/2001 | Summers et al. | ........... | 382/128 |
| 6,442,235 B2 * | 8/2002 | Koppe et al. | ............ | 378/62 |
| 6,480,732 B1 * | 11/2002 | Tanaka et al. | .......... | 600/425 |
| 6,512,807 B1 * | 1/2003 | Pohlman et al. | .......... | 378/4 |
| 6,741,880 B1 * | 5/2004 | Foo et al. | ............. | 600/419 |
| 2001/0031920 A1 * | 10/2001 | Kaufman et al. | .......... | 600/431 |
| 2002/0168618 A1 * | 11/2002 | Anderson et al. | .......... | 434/262 |

FOREIGN PATENT DOCUMENTS

EP    0 860 696 A2    8/1998

* cited by examiner

Primary Examiner—Angela D. Sykes
Assistant Examiner—William C. Jung

(57) ABSTRACT

The invention relates to a method of imaging a vascular tree that yields additional information concerning the vascular tree. To this end, a sequence of clusters is determined from spatially coherent voxels in the three-dimensional image of the vascular tree, the sequence of said clusters corresponding to the flow direction of the blood or the contrast medium in said vascular tree.

14 Claims, 5 Drawing Sheets

METHOD OF IMAGING THE BLOOD FLOW IN A VASCULAR TREE

BACKGROUND

The invention relates to a method of imaging the blood flow in a vascular tree of an object to be examined, as well as to an X-ray device for carrying out such a method.

EP 860 696 A2 describes the formation of a series of X-ray projection images, that is, from different projection directions, of an object to be examined whose vascular tree is filled with a contrast medium. A three-dimensional image that contains a representation in space of the vascular tree is derived from said (two-dimensional) X-ray projection images by means of a known reconstruction algorithm.

For various applications, such as the analysis of pathologies of the cerebral vascular tree, however, further information is required in addition to the image of the vascular tree.

SUMMARY OF THE INVENTION

Therefore, it is an object of the present invention to provide a method that offers additional information, and also to provide an X-ray device for carrying out such a method.

This object is achieved in accordance with the invention by means of a method of imaging the blood flow in a vascular tree of an object to be examined, which method includes the steps of:

a) forming a series of X-ray projection images of the object to be examined from different projection directions, b) reconstructing a three-dimensional image that contains an image of the vascular tree from the X-ray projection images, c) determining a series of clusters from spatially coherent voxels in the three-dimensional image, at least one cluster that is defined by the direction of the blood flow being determined as from a start cluster of the vascular tree, said cluster itself acting as the starting point for the determination of at least one next cluster in the sequence and at least some of its voxels adjoining the voxels of the start cluster and of the next cluster, and for each new cluster of the sequence there being determined the subsequent cluster.

Because the next clusters in the direction of blood flow in the vascular tree are determined as from a predetermined voxel or cluster (start cluster), additional information is obtained that offers an examiner an impression of the propagation of the contrast medium or the blood flow in the vascular tree. In another embodiment practicing aspects of the present invention, the sequence of clusters determined can be made recognizable in an image, for example, by reproducing the sequence of clusters in different colors or by highlighting, in a dynamic representation, the clusters of the vascular tree successively in conformity with the sequence of clusters determined.

Even though more thorough analysis of the vascular tree is thus possible, these steps alone does not suffice to derive information concerning the actual progression in time of the blood flow in the vascular tree. In the previous, non-prepublished German patent application 10000185.8 in the name of applicant (PHDE000001), therefore, it is proposed to derive information concerning the propagation of the contrast medium in the vascular tree from a series of X-ray projection images that represent the vascular tree in different phases of inflow of a contrast medium, and to determine the times of arrival of the so-called contrast medium bolus (being the foremost part of the contrast medium as seen in the direction of blood flow) in the various parts of the vascular tree.

The problems that may then occur, for example, due to inaccurate determination of the time of arrival or due to the fact that vessels overlap in the projection images, can be solved. For example, in another embodiment practicing an aspect of the present invention, the temporal information obtained is combined with the information concerning the clusters of the vascular tree. An additional advantage resides in the fact that the times of arrival are not determined for individual voxels, but for clusters that usually consist of a number of voxels. The noise in the X-ray projection images then has less effect on the determination of the times of arrival.

The temporal information obtained and the information concerning the clusters of the vascular tree can be combined in various ways. For example, a cluster cannot have a time of arrival that is earlier than a cluster that precedes the relevant cluster in the sequence, so that correction of the time of arrival determined for the contrast medium bolus is possible already by means of this plausibility criterion. Such inaccuracies, however, can also be corrected by filtering in conformity with another embodiment practicing an aspect of the present invention wherein, the times of arrival of the sequence of clusters determined are subjected to median filtering for the purpose of modification.

Yet another embodiment practicing an aspect of the present invention enables the correct time of arrival to be assigned to clusters that overlap in the projection image. For example, an overlapping projection of clusters in the X-ray projection images and multiple arrival of the contrast medium bolus in this projection, the times of arrival are assigned to the associated clusters in the three-dimensional image in dependence on the times of arrival determined each time for the respective neighboring clusters in the vascular tree.

When the times of arrival thus determined are differentiated in the direction of the center lines of the vessels of the vascular tree, speed information is obtained that can also be reproduced (for example in color) in the three-dimensional image of the vascular tree; such information enables additional interpretations, for example, in conjunction with the radius of the vessel. For example, a high speed and a small diameter of the vessel in a given cluster may be an indication of a stenosis.

It would be possible in principle to derive the information concerning the progression in time of the blood flow from the same series of X-ray projection images as that wherefrom the three-dimensional image of the vascular tree is reconstructed; this would have the advantage that the radiation dose for the patient is not increased. However, in that case the inflow of the contrast medium cannot be tracked with the necessary accuracy. This drawback can be avoided by means in which two series of X-ray projection images are formed for the extraction of the spatial information and of the temporal information.

In addition to the vascular tree other structures are also reproduced in the three-dimensional image that is derived from the series of X-ray projection images, for example, bones that could disturb the evaluation. This drawback can be avoided by means in which the vascular tree is segmented. In the simplest case this segmentation may consist in that all voxels in the three-dimensional image that are below a given value are assigned to the vascular tree and the reproduction of all other voxels is suppressed.

An X-ray device for carrying out aspects of the method in accordance with the invention comprises an imaging unit (1) with an X-ray source (12) and an X-ray detector (13) for forming a series of X-ray projection images ($D_i$) of the object (3) to be examined from different projection directions, and an arithmetic unit (19) for reconstructing a three-dimensional image that contains a rendition of the vascular tree from the X-ray projection images ($D_i$) and for determining a sequence of clusters from spatially coherent voxels in the three-dimensional image, where at least one cluster that is defined by the direction of the blood flow is determined as from a start cluster of the vascular tree, said cluster itself acting as the starting point for the determination of at least one next cluster in the sequence and at least some of its voxels adjoining the voxels of the start cluster and of the next cluster, and for each new cluster of the sequence there being determined the subsequent cluster. When parts of the vascular tree extend in the projection direction during the acquisition of the series of X-ray projection images that represent the various phases of the inflow of a contrast medium, accurate analysis of such parts of the vascular tree is not possible. This drawback can be avoided when use is made of two X-ray systems with projection directions that are preferably 90° offset relative to one another.

The following description, claims and accompanying drawings set forth certain illustrative embodiments applying various principles of the present invention. It is to be appreciated that different embodiments applying principles of the invention may take form in various components, steps and arrangements of components and steps. These described embodiments being indicative of but a few of the various ways in which some or all of the principles of the invention may be employed in a method or apparatus. The drawings are only for the purpose of illustrating an embodiment of an apparatus and method applying principles of the present invention and are not to be construed as limiting the present invention.

BRIEF DESCRIPTION OF THE DRAWINGS

The foregoing and other features and advantages of the present invention will become apparent to those skilled in the art to which the present invention relates upon consideration of the following detailed description of apparatus applying aspects of the present invention with reference to the accompanying drawings, wherein.

DETAILED DESCRIPTION

Figure 1:
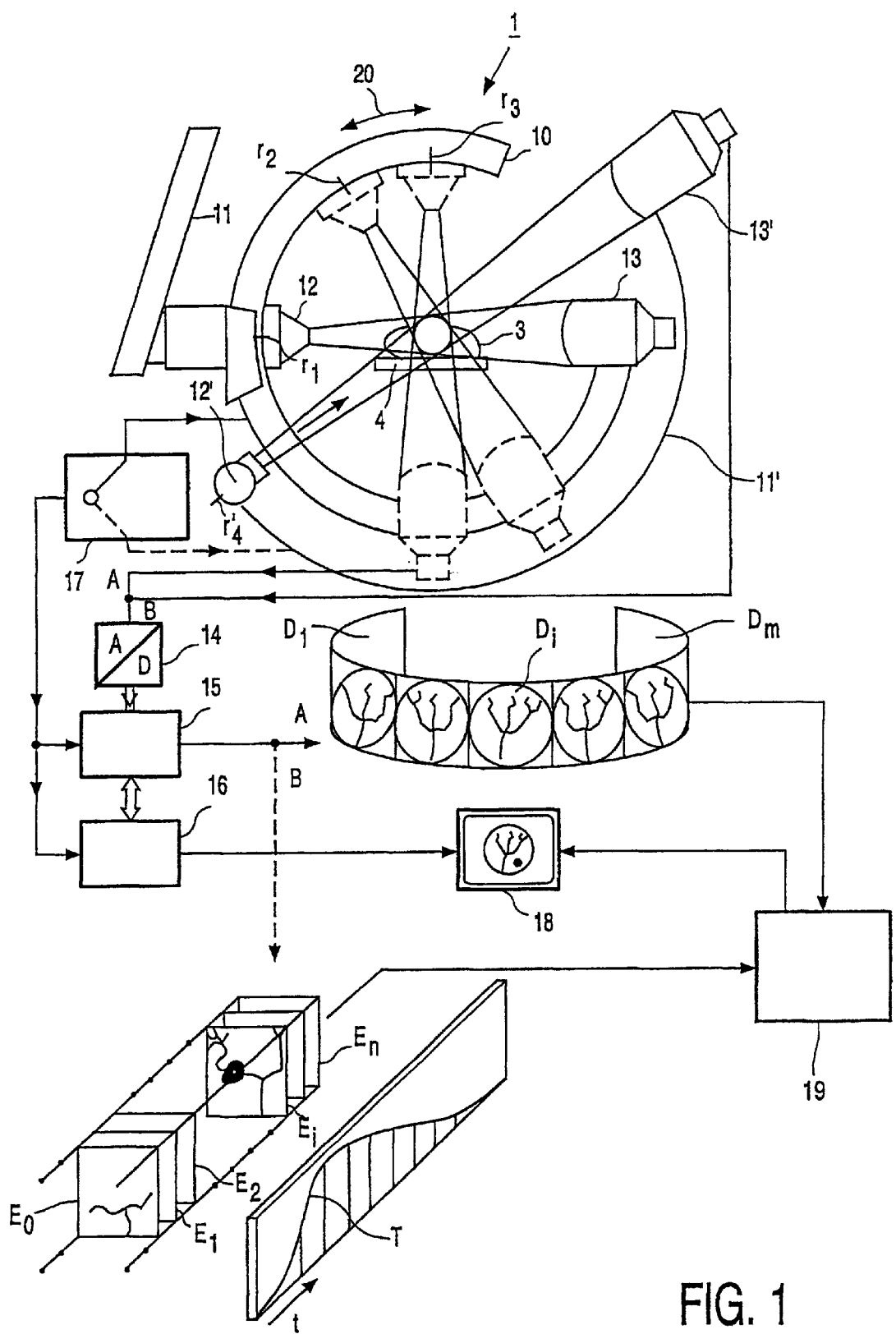
FIG. 1 is a diagrammatic representation of an X-ray device for carrying out the method in accordance with the invention.

FIG. 1 shows an X-ray device 1 that serves for the formation of two-dimensional X-ray images, or X-ray projection images, of an object 3 to be examined, for example, a patient who is arranged on a table 4. The X-ray device includes an X-ray source 12 and an X-ray detector 13 that are mounted so as to face one another on a C-arm 10 which itself is mounted on a stand 11 that is only partly shown. The C-arm 10 on the one hand can be pivoted about a horizontal axis while on the other hand it can be rotated, by means of a motor drive, for example, through 180° about its center in the direction of the double arrow 20. This movement enables the formation of a multitude of X-ray images that represent the object 3 to be examined from different reproducible projection directions $r_1$, $r_2$, $r_3$ of the X-ray system 12, 13.

There are also provided a second X-ray source 12' and a second X-ray detector 13' that are mounted on a mounting device 11' and are capable of forming projection images of the object 3 to be examined from a fixed X-ray position $r'_4$. Each of the X-ray detectors 13, 13' may be formed by an X-ray intensifier whereto there is connected a television chain whose output signals are digitized by an analog-to-digital converter 14 so as to be stored in a memory 15.

The X-ray projection images $D_1 \ldots D_i \ldots D_m$ that are acquired by the imaging unit 12, 13 from different positions $r_1, \ldots r_i, \ldots r_n$ (only the positions $r_1$, $r_2$, $r_3$ thereof being explicitly shown in the drawings) can be processed by an image processing unit 16 so as to be displayed, individually or as a series of images, on a monitor 18. The X-ray projection images $E_0, E_1, E_2 \ldots E_n$ that are acquired by the imaging unit 12', 13' from the fixed X-ray position $r'_4$ at discrete instants during the inflow of a contrast medium can also be processed by the image processing unit 16 so as to be displayed on the monitor 18. The individual components of the X-ray device are controlled by means of a control unit 17.

There is also provided an arithmetic unit 19 which receives the X-ray projection images and derives therefrom the information that is required for the reproduction of the temporal and spatial progression of the contrast medium. This information can again be displayed on the monitor 18.

Figure 2:
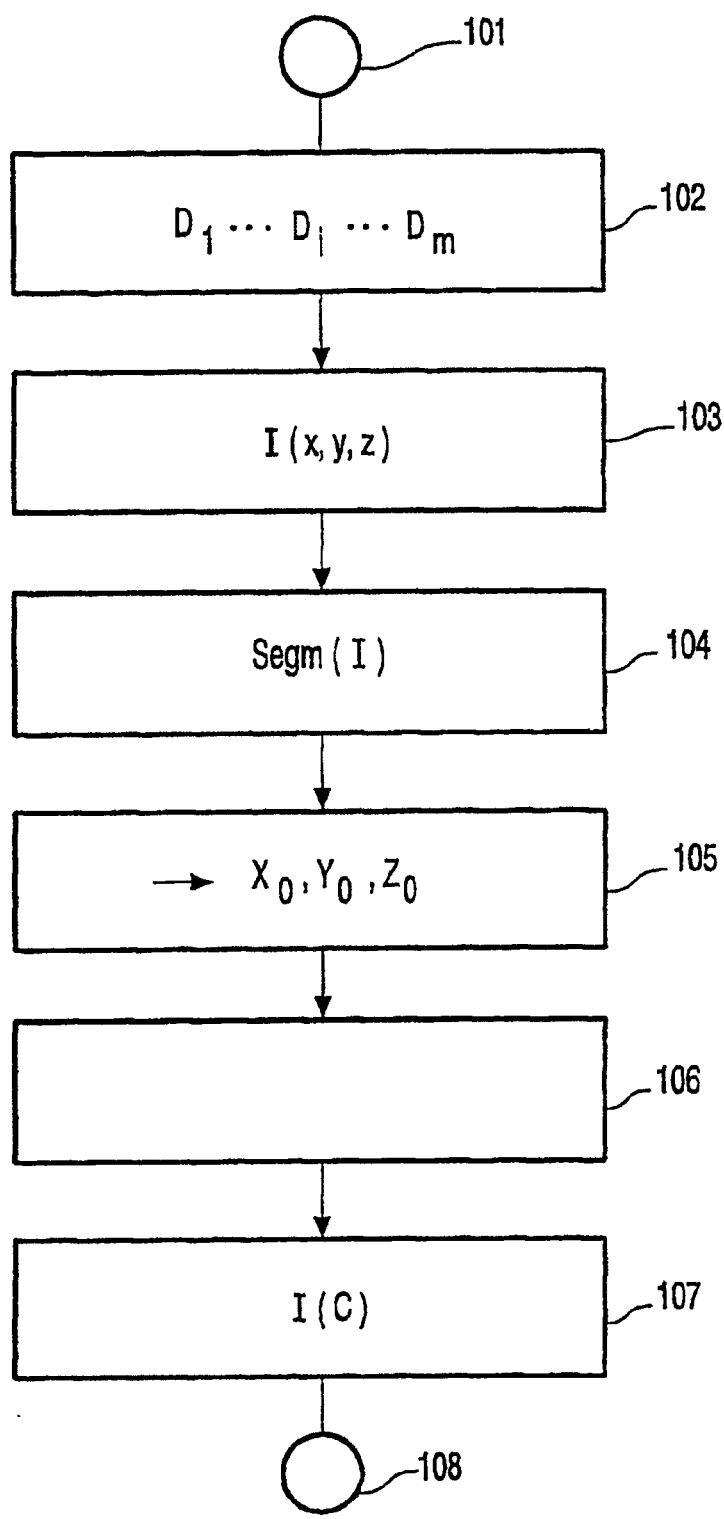
FIG. 2 shows a flow chart of the method in accordance with the invention.

The invention will be described in detail hereinafter with reference to the flow chart that is shown in FIG. 2. After the initialization (step 101), a (first) series of X-ray projection images $D_1 \ldots D_i \ldots D_m$ are acquired with different projection directions while the vascular tree is filled with a contrast medium (step 102). Subsequently, in the step 103 a three-dimensional image is reconstructed from the series of (two-dimensional) X-ray projection images. In this respect it is assumed that the position and the orientation of the X-ray source 12 and an X-ray detector 13 are exactly known for each projection image (for example, on the basis of a preceding calibration measurement).

The reconstructed three-dimensional image not only shows the vascular tree (filled with contrast medium), but also other structures such as bones. Therefore, in the step 104 the three-dimensional image is segmented in such a manner that it shows only the vascular tree while all other structures are suppressed. In the simplest case such segmentation can be performed by way of a thresholding operation that assigns all voxels that have a comparatively high absorption value to the vascular tree and suppresses the reproduction of all other voxels. Use may alternatively be made of a different segmentation method (for example, a method capable of detecting line-shaped structures) that produces more accurate segmentation but usually requires more calculation effort.

In the step 105 a start voxel (or a group of coherent voxels) is selected, that is, preferably at an area of the vascular tree where the contrast medium enters the reconstructed region of the vascular tree. Such selection can be performed interactively by a user, but also automatically.

Figure 3:
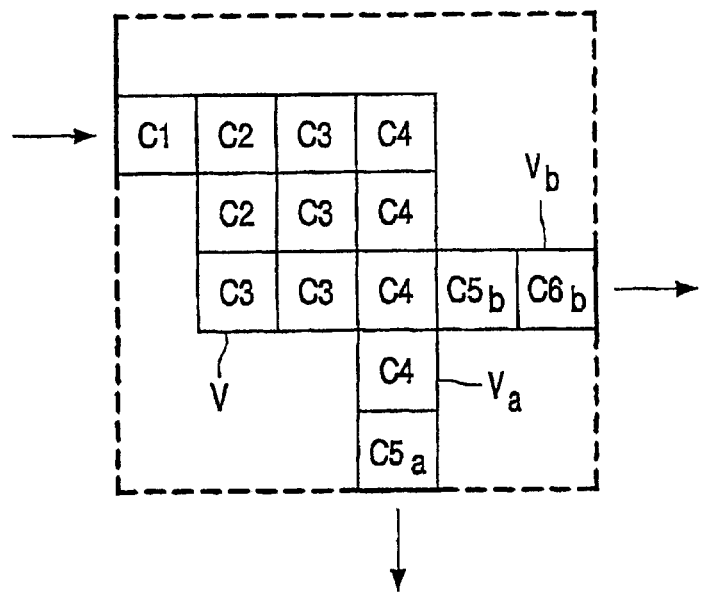
FIG. 3 illustrates the determination of successive clusters.

Proceeding from said start voxel, the vascular tree is subdivided into sections in the step 106, said sections being referred to hereinafter as clusters. Each cluster comprises those voxels of a vascular tree that neighbor a voxel of the preceding cluster. This procedure will be described in detail hereinafter with reference to FIG. 3 which is a simplified diagrammatic representation of a part of the vascular tree V. Each voxel therein is symbolized by a square. The start cluster 1 consists of a single voxel and is denoted by the reference C1.

The next cluster C2 is formed by the voxels that adjoin the voxel (voxels) of the preceding cluster (in this case the start cluster C1) and that belong to the vascular tree; in the two-dimensional case up to eight voxels may adjoin a single voxel while in the three-dimensional case as many as 26 voxels may adjoin such a single voxel. In conformity with FIG. 3, two voxels belong to the cluster C2. In the vascular tree V these voxels are adjoined by four voxels that form the next cluster C3. Even though the voxel C1 also adjoins the voxels of this cluster, it is not added to the new cluster because it already belongs to the preceding cluster generation. The four voxels of the cluster C3 in the vascular tree V again have four neighboring voxels that form the cluster C4. One of these voxels is present in one of the two branches $V_a$ and $V_b$ of the vascular tree V.

The voxels of the cluster C4 are adjoined by two voxels $C5_a$ and $C5_b$ in the branches $V_a$ and $V_b$ of the vascular tree. As opposed to the preceding clusters, the voxels of this cluster generation are not spatially coherent. Therefore, they form separate clusters even though they belong to the same cluster generation. The voxel $C6_b$ is then determined as the next cluster of the sequence (in the branch $V_b$). The entire vascular tree is thus subdivided into a sequence of adjoining clusters in the step 106.

This subdivision by itself offers a better insight into the structure of the vascular tree that can be used in the step 107, for example, in order to reproduce the various cluster generations in different color shades in one or more two-dimensional images. The method is subsequently terminated (step 108).

Figure 4:
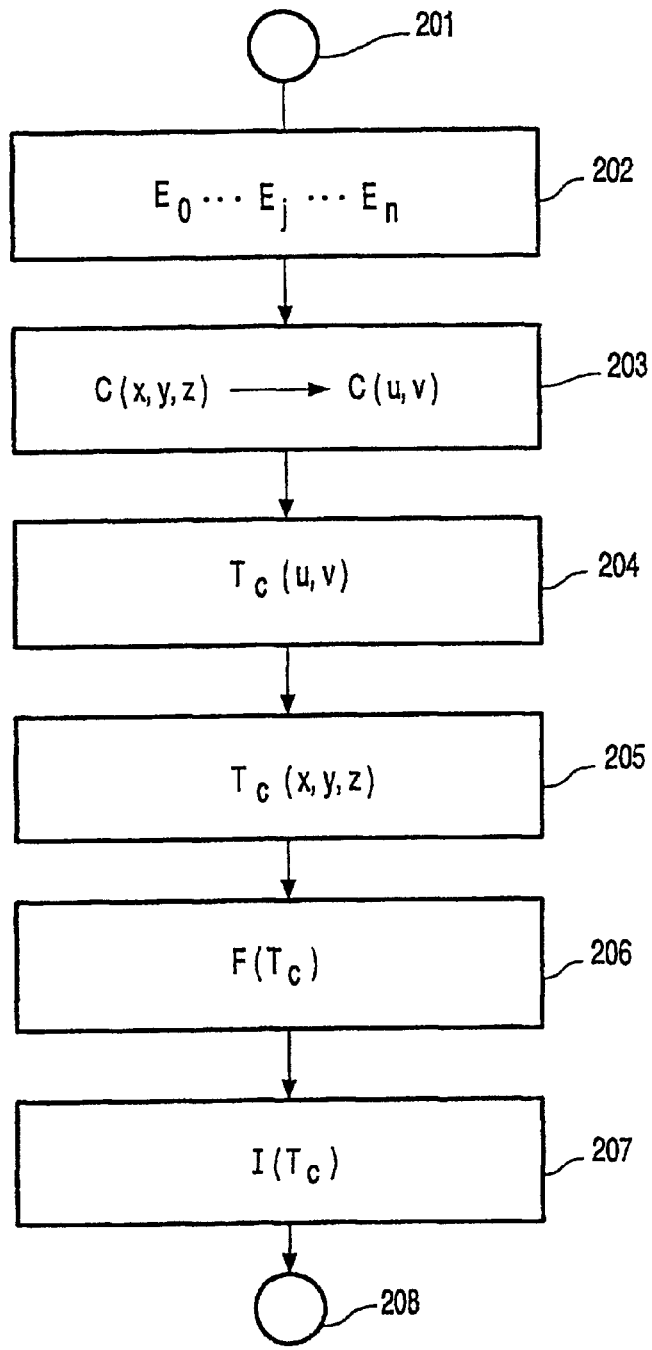
FIG. 4 shows a flow chart that enables the additional evaluation of temporal information.

Instead of reproducing the generation sequence of the clusters, however, in the step 107 the information contained in the cluster formation can be combined with the temporal information that can be derived from the inflow of the contrast medium. This will be described in detail hereinafter with reference to the flow chart that is shown in FIG. 4. After the initialization in the step 201, in the step 202 a (second) series of projection images $E_0, E_1, E_2 \ldots E_j \ldots E_n$ (FIG. 1) is formed from a fixed projection direction, for example, by means of the X-ray system 12', 13'. This second series is advantageously acquired separately in time from the first series, for example, after the first series, because for the first series it is important that the vascular tree is reproduced while filled with contrast medium from all projection directions, whereas for the second series it is important to track the inflow into the vascular tree in time. In this case it is not necessary either to provide a second X-ray system 12' and 13' for this purpose; the second series can also be acquired by means of the (single) X-ray system 12 and 13.

For the acquisition of this second series the projection direction should be chosen to be such that the branches of the vascular tree overlap as little as possible. The surface on which the vascular tree is projected becomes maximum for this projection direction. This projection direction can be determined, for example by calculating, while using the three-dimensional image, the projection images that will occur when the vascular tree (characterized by a three-dimensional data set) is projected in a given direction.

Even when the best possible projection direction is selected, however, it may still occur that parts of the vascular tree extend in the projection direction, so that the propagation of the contrast medium in this part cannot be tracked. This drawback can be avoided by forming at the same time images from a second direction that extends perpendicularly to the first projection direction, that is, by means of the X-ray system 12, 13. This further projection direction is characterized by the position $r_2$ of the X-ray source 12 in FIG. 1.

The number of projection images acquired by means of this step of the method during the inflow of the contrast medium determines the temporal resolution; this means that the number of different times of arrival of the contrast medium bolus corresponds to the number of projection images. When this number is significantly smaller than the number of cluster generations, it is advantageous to form a respective extended cluster from a plurality of clusters. The determination of the time of arrival of the contrast medium bolus for an (extended) cluster instead of for a single voxel not only results in a reduction of the necessary calculation effort, but also offers the advantage that the time of arrival then determined is less subject to noise.

During the subsequent step 203 it is examined which voxels of the two-dimensional projection images are covered each time by the projection of the possibly extended cluster. To this end, the position $C(u,v)$ of the cluster $C(x,y,z)$ of the three-dimensional vascular tree, as determined in the step 106, is calculated in a two-dimensional projection image, that is, on the basis of the projection geometry of the system 12'/13' during the acquisition of the second series and of the position of the vascular tree relative to the system that results from the reconstruction of the three-dimensional image (step 103).

Figure 5:
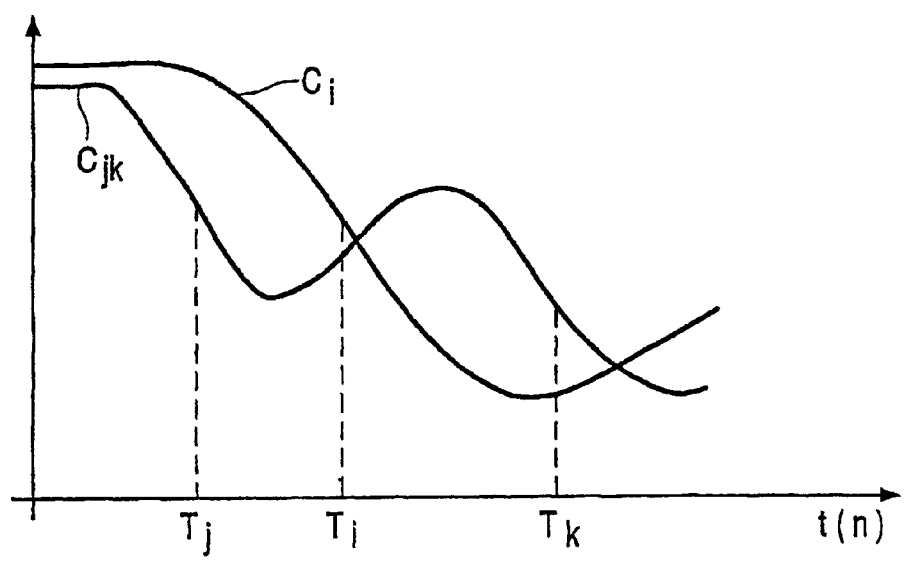
FIG. 5 shows the variation in time of the brightness in various clusters.

The variation in time of the brightness value (averaged over the surface area of the projection $C(u,v)$ of the cluster, is then determined for each cluster in the step 204. FIG. 5 shows the variation in time of the spatially averaged brightness for a cluster. The brightness curve $C_i$ for the cluster bearing the same name reveals that the brightness decreases from a maximum value prior to the inflow to a minimum value and that, after the outflow of the contrast medium, it strongly increases again. The instant $T_p$ at which the variation of the brightness curve $C_i$ is strongest is evaluated (again in the step 204) as the time of arrival $T_c(u,v)$ of the contrast medium bolus in the relevant cluster.

Figure 6:
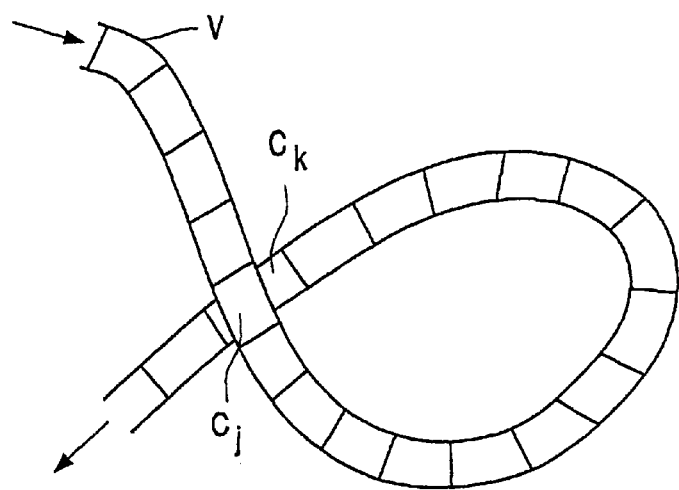
FIG. 6 shows an overlapping part of the vascular tree.

During the subsequent step 205 the time of arrival determined is assigned to the three-dimensional image of the vascular tree. When the relative cluster is not masked by other clusters, such assignment is simple and unambiguous. Assignment becomes more difficult when two or more clusters overlap in the projection images. FIG. 6 shows such a case; it shows a part of the vessel of the vascular tree V that is subdivided into clusters of which the clusters $C_j$ and $C_k$ overlap one another. The associated brightness variation is represented by the curve $C_{jk}$ in FIG. 5. It appears that the brightness first decreases, a first time of arrival $T_j$ then occurring in the region of the largest decrease in time. Subsequently, the brightness increases again, after which it decreases once more, resulting in a second time of arrival $C_k$. The two times of arrival thus determined can be correctly assigned to the two clusters $C_j$ and $C_k$ on the basis of the knowledge of the cluster generations in the vascular tree V.

Figure 7:
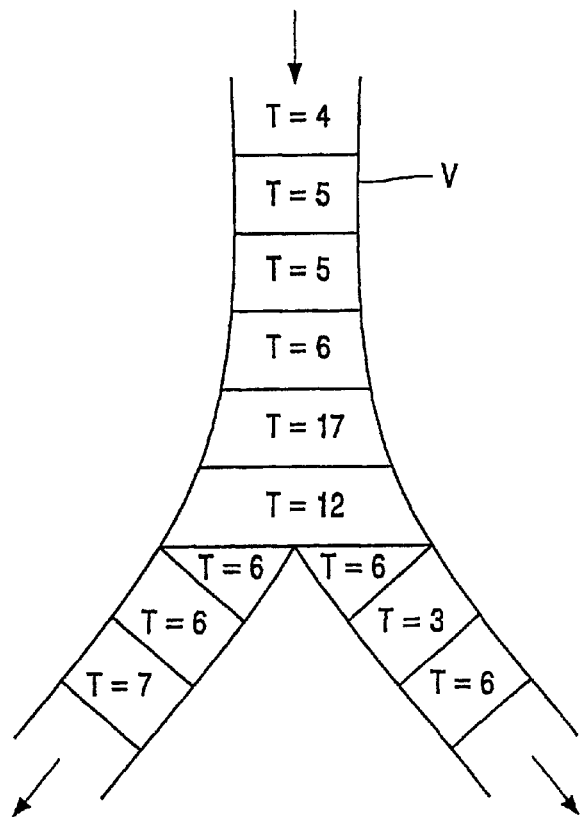
FIG. 7 shows the times of arrival determined for successive clusters of a part of the vascular tree.

When a time of arrival has been assigned to each cluster, successive clusters should have similar times of arrival. In practice, however, there may be a small percentage of "outliers" where the time of arrival is not compatible with that of the neighboring clusters in the sequence. An example in this respect is shown in FIG. 7 in which the times of arrival are determined for each cluster (in relative units) are plotted. It appears that there are two outliers in the region of the bifurcation.

These outliers are eliminated in the step 206, for example, by median filtering over the sequence of times of arrival assigned to the sequence of clusters. When a filter kernel of each time five values is used for the median filter (the size of the kernel determines the number of successive outliers that can still be corrected), such outliers can be eliminated. For the cluster having the time of arrival T=17, for example, there are the values 5, 6, 17, 12, (6+6)/2 (it being assumed that the times of arrival of the clusters that are situated behind the bifurcation and belong to the same cluster generation are averaged). When these values are sorted in an order of magnitude, the value T=6 is obtained as the median value for the relevant cluster. For the cluster for which the time of arrival T=12 is determined, the times of arrival of the neighboring clusters produce the sequence 6, 17, 12 (6+6)/2 (6+3)/2 that again yields a median value of 6 that replaces the outlier T=12.

The inflow of the contrast medium can be visualized in the step 207. For example, the different times of arrival can be represented by different color shades of the clusters in the three-dimensional image of the vascular tree. Instead of this static display, dynamic display is also possible; for the times at which projection images have been acquired in the step 202 the clusters that have already been passed by the contrast medium bolus at the relevant instant are highlighted in a suitable manner. When this operation is performed for all instants, a dynamic representation of the contrast medium inflow or the blood flow is obtained.

Other possibilities for display also exist. For example, the propagation speed of the contrast medium or the blood in the vascular tree can be determined and reproduced, for example, in color by differentiation of the times of arrival along the center lines of the vessels. When the speed information is supplemented with information concerning the dimensions at the relevant area, additional information can be provided. For example, a high speed in combination with a small vessel diameter may indicate a stenosis.

The method is terminated subsequent to this evaluation (208). The invention is of course not limited to the described or shown embodiments, but generally extends to any embodiment, which falls within the scope of the appended claims as seen in light of the foregoing description and drawings. While a particular feature of the invention may have been described above with respect to only one of the illustrated embodiments, such features may be combined with one or more other features of other embodiments, as may be desired and advantageous for any given particular application. From the above description of the invention, those skilled in the art will perceive improvements, changes and modification. Such improvements, changes and modification within the skill of the art are intended to be covered by the appended claims.

Having described a preferred embodiment of the invention, the following is claimed:

1. A method of imaging the blood flow in a vascular tree of an object (3) to be examined, which method comprising the steps of:
   a) forming a series of X-ray projection images ($D_i$) of the object to be examined (3) from different projection directions,
   b) reconstructing a three-dimensional image that contains an image of the vascular tree from the X-ray projection images ($D_i$), and
   c) determining a sequence of clusters ($C_1, C_2, C_3, \ldots$) each including a plurality of spatially coherent voxels of the vascular tree in the three-dimensional image, at least one cluster ($C_2$) that is defined by the direction of the blood flow being determined as from a start cluster ($C_1$) of the vascular tree, said cluster itself acting as the starting point for the is determination of at least one next cluster ($C_3$) in the sequence and at least some of its voxels adjoining the voxels of the start cluster and of the next cluster, and for each new cluster of the sequence there being determined the subsequent cluster.

2. A method as claimed in claim 1, wherein the clusters ($C_1, C_2, C_3, \ldots$) are displayed on a display unit in such a manner that the sequence of clusters determined can be recognized.

3. A method as claimed in claim 1, wherein prior to the determination of the clusters, the three-dimensional image is segmented in such a manner that essentially only the vascular system is reproduced in the image.

4. A method of imaging the blood flow-in a vascular tree of an object to be examined, which method includes the steps of:
   a) forming a series of X-ray projection images of the object to be examined from different projection directions,
   b) reconstructing a three-dimensional image that includes an image of the vascular tree from the X-ray projection images,
   c) determining a sequence of clusters in the three-dimensional image, at least one cluster being defined by the direction of the blood flow determined as from a start cluster of the vascular tree, the cluster acting as the start cluster for the determination of at least one next cluster in the sequence and at least some of its voxels adjoining the voxels of the start cluster and of the next cluster;
   d) forming a series of X-ray projection images that reproduce the vascular tree in different phases of inflow of a contrast medium,
   e) determining the areas in the X-ray projection images on which the voxels of the clusters have been projected,
   f) assigning the times of arrival of a contrast medium bolus, which times follow for said areas from the variation in time of the grey values in the X-ray projection images, to the clusters in the three-dimensional image, and
   g) modifying the times of arrival in dependence on the sequence of clusters determined.

5. A method as claimed in claim 4, in which the times of arrival of the sequence of clusters determined are subjected to median filtering for the purpose of modification.

6. A method as claimed in claim 4, in which in the case of an overlapping projection of clusters in the X-ray projection images and multiple arrival of the contrast medium bolus in this projection, the times of arrival are assigned to the associated clusters in the three-dimensional image in dependence on the times of arrival determined each time for the respective neighboring clusters in the vascular tree.

7. A method as claimed in claim 4, wherein speed information is derived from the times of arrival determined for the clusters of the vascular tree.

8. A method as claimed in claim 4, wherein at least one series of X-ray projection images that reproduces the vascular system in different phases of a contrast medium inflow is formed from a fixed projection direction.

9. A method as claimed in claim 8, wherein that the series of X-ray projection images is formed from a projection direction for which the surface area covered by the vascular tree has a maximum value.

10. An X-ray device comprising:

an imaging unit (1) with an X-ray source (12) and an X-ray detector (13) for forming a series of X-ray projection images ($D_i$) of the object (3) to be examined from different projection directions, and an arithmetic unit (19) for reconstructing a three-dimensional image that contains a rendition of the vascular tree from the X-ray projection images ($D_i$) and for determining a sequence of clusters each cluster including a plurality of spatially coherent voxels of the vascular tree in the three-dimensional image, where at least one cluster that is defined by the direction of the blood flow is determined as from a start cluster of the vascular tree, said cluster itself acting as the starting point for the determination of at least one next cluster in the sequence and at least some of its voxels adjoining the voxels of the start cluster and of the next cluster, and for each new cluster of the sequence there being determined the subsequent cluster.

11. An X-ray device as claimed in claim 10, wherein the imaging unit includes a first X-ray source (12) and a first X-ray detector (13) for acquiring a series of two-dimensional X-ray images from a first projection direction, and a second X-ray source (12') and a second X-ray detector (13') for the simultaneous acquisition of a series of two-dimensional X-ray images from a second projection direction that encloses an angle of preferably 90° relative to the first projection direction.

12. An X-ray device comprising:

an imaging unit with one or more X-ray sources and a corresponding one or more X-ray detectors for forming a series of directionally varying X-ray projection images ($D_i$) of the object to be examined from different projection directions and for forming a series of temporally varying X-ray projection images ($E_i$) acquired over inflow of a contrast medium bolus into a vascular tree of the object; and an arithmetic unit for:

reconstructing a three-dimensional image that contains a rendition of the vascular tree from the X-ray projection images ($D_i$), determining a plurality of clusters comprising spatially coherent vascular tree voxels of the three-dimensional image wherein each cluster is spatially adjacent to at least one other cluster, determining the areas in the temporally varying X-ray projection images on which the voxels of the clusters have been projected, and assigning the times of arrival of the contrast medium bolus, which times follow for said areas from the variation in time of the grey values in the X-ray projection images, to the clusters in the three-dimensional image.

13. A method of imaging blood flow in a vascular tree, the method comprising:

acquiring a three-dimensional image of the vascular tree;

dividing the three-dimensional image of the vascular tree into clusters of voxels;

acquiring a plurality of projection images during inflow of a contrast agent into the vascular tree; and assigning a time of arrival value to each cluster based on the projection images.

14. The method as set forth in claim 13, wherein the assigning of a time of arrival includes:

associating portions of the projection images with corresponding clusters;

computing a temporal variation in the intensity of each projection image portion;

determining a time of arrival for each projection image portion based on the temporal variation in the intensity of that image portion across the plurality of projection images; and assigning the time of arrival for each projection image portion to the corresponding cluster.

* * * * *